(12) United States Patent
Araújo et al.

(10) Patent No.: US 11,650,657 B2
(45) Date of Patent: May 16, 2023

(54) COMMUNICATING OLFACTORY CONTENT

(71) Applicant: Telefonaktiebolaget LM Ericsson (publ), Stockholm (SE)

(72) Inventors: José Araújo, Stockholm (SE); Lars Andersson, Solna (SE); Bengt Lindoff, Bjärred (SE); Zeid Al-Husseiny, Järfälla (SE)

(73) Assignee: TELEFONAKTIEBOLAGET LM ERICSSON (PUBL), Stockholm (SE)

( * ) Notice: Subject to any disclaimer, the term of this patent is extended or adjusted under 35 U.S.C. 154(b) by 89 days.

(21) Appl. No.: 17/042,752

(22) PCT Filed: Mar. 28, 2018

(86) PCT No.: PCT/SE2018/050336
§ 371 (c)(1),
(2) Date: Sep. 28, 2020

(87) PCT Pub. No.: WO2019/190369
PCT Pub. Date: Oct. 3, 2019

(65) Prior Publication Data
US 2021/0026442 A1    Jan. 28, 2021

(51) Int. Cl.
*G06F 3/01*  (2006.01)
*A63F 13/28* (2014.01)
(Continued)

(52) U.S. Cl.
CPC ............ *G06F 3/011* (2013.01); *A61B 5/0022* (2013.01); *A61B 5/4011* (2013.01); *A63F 13/28* (2014.09);
(Continued)

(58) Field of Classification Search
CPC ........ G06F 3/011; G06F 3/016; G06F 3/0484; G06F 2203/0381; G06F 3/0482; A63F 13/28; A61B 5/4011
See application file for complete search history.

(56) References Cited

U.S. PATENT DOCUMENTS 5,398,070 A    3/1995 Lee
5,887,118 A    3/1999 Huffman et al.
(Continued)

FOREIGN PATENT DOCUMENTS

| JP | 2016199452 A1 | 2/2018 |
| WO | 2016199452 A1 | 12/2016 |
| WO | 2017165295 A1 | 9/2017 |

OTHER PUBLICATIONS

International Search Report and the Written Opinion of the International Searching Authority, issued in corresponding International Application No. PCT/SE2018/050336, dated Jan. 25, 2019, 13 pages.
(Continued)

*Primary Examiner* — Robert J Michaud
(74) *Attorney, Agent, or Firm* — Rothwell, Figg, Ernst & Manbeck, P.C.

(57) ABSTRACT

It is provided method for communicating olfactory content. The method is performed in an olfactory device and comprises the steps of: obtaining olfactory content to be rendered at a recipient device; identifying an olfactory state at the recipient device; determining an adjustment of at least one olfactory component, based on the identified olfactory state, to render the olfactory content; and triggering the recipient device to perform the adjustment of at least one olfactory component.

16 Claims, 4 Drawing Sheets

(51) Int. Cl.
 *A61B 5/00* (2006.01)
 *H04L 67/131* (2022.01)
(52) U.S. Cl.
 CPC .... *H04L 67/131* (2022.05); *A61B 2562/0204* (2013.01)

(56) References Cited

U.S. PATENT DOCUMENTS

| | | |
|---|---|---|
| 6,628,204 B1 | 9/2003 | Ito |
| 2014/0365601 A1 | 12/2014 | Natkunanathan |
| 2017/0124797 A1 | 5/2017 | Chan et al. |
| 2017/0131689 A1 | 5/2017 | Chan et al. |
| 2017/0364605 A1 | 12/2017 | Sobel et al. |
| 2018/0110457 A1* | 4/2018 | Smith .................. A61B 5/4011 |
| 2018/0144033 A1* | 5/2018 | Hirata .................... A63F 13/79 |

OTHER PUBLICATIONS

Nakamoto et al. "Selection Method of Odor Components for Olfactory Display Using Mass Spectrum Database" IEEE Virtual Reality Conference, Mar. 2009, pp. 159-162.

Murray et al. "Olfaction-Enhanced Multimedia: A Survey of Application Domains, Displays, and Research Challenges" ACM Computing Surveys, vol. 48, No. 4, Article 56, Publication date: May 2016, 34 pages.

McGookin et al. "Hajukone: Developing an Open Source Olfactory Device" Late-Breaking Work: Extending User Capabilities, 2016, pp. 1721-1728.

Ko et al. "Bioelectronic nose and its application to smell visualization" Journal of Biological Engineering (2016) 10:17, 9 pages.

Wilson et al. "Applications and Advances in Electronic-Nose Technologies" Sensors 2009, 9, pp. 5099-5148.

\* cited by examiner

COMMUNICATING OLFACTORY CONTENT

CROSS REFERENCE TO RELATED APPLICATION(S)

This application is a 35 U.S.C. § 371 National Phase Entry Application from PCT/SE2018/050336, filed Mar. 28, 2018, designating the United States, the disclosure of which is incorporated herein by reference in its entirety.

TECHNICAL FIELD

The invention relates to methods, olfactory devices, olfactory content transmitters, computer programs and computer program products for communicating olfactory content.

BACKGROUND

Mixed reality (MR) and Virtual Reality (VR) are foreseen to become an integral technology in the networked society and potently disrupt the consumer electronics market. Several companies believe that there will be a potential next platform shift to MR and VR, which can give growth to $120 billion by 2020. Of this, MR is the bigger opportunity with a $90 billion share. MR hardware is likely drive the market, followed by augmented commerce, data, voice, video, and enterprise. As an example, the 2016 phenomenon of Pokemon Go has truly put forward the advantages of MR in the way people interact with each other and with video games.

Several MR and VR devices have been launched in the last years by companies as Oculus, HTC Vive, Microsoft, Google, Sony, among many others.

As the MR and VR fields mature with improved hardware and software solutions, several companies are now investing on enhancing the user experience by introducing devices with additional sensing and actuation modalities. As an example, several new solutions to enable the sense of touch via haptic sensors and actuators are being investigated and deployed together with MR and VR devices.

In order to further enhance the user experience, solutions providing users with the sense of smell (also known as olfactory sensing) are developed, which can be combined with visual, audio and haptic experiences or experienced on their own.

Digital scent technology is expected to dramatically increase in impact and importance. The companies Scentcom and Inhalió provide a device which releases a wide range of smells to a user using a printer-like dry air cartridge technology. The applications for these devices range from gaming, virtual reality application, e-commerce and automotive. The company Feelreal has developed a VR mask which releases smells. The company Scent Sational Technologies offers various solutions for dispensing smells. On the sensing side, the company Aryballe has created a digital nose to detect and identify odours.

SUMMARY

It is an object to provide an improved way of sharing olfactory content.

According to a first aspect, it is provided method for communicating olfactory content. The method is performed in an olfactory device and comprises the steps of: obtaining olfactory content to be rendered at a recipient device; identifying an olfactory state at the recipient device; determining an adjustment of at least one olfactory component, based on the identified olfactory state, to render the olfactory content; and triggering the recipient device to perform the adjustment of at least one olfactory component.

The step of determining an adjustment may comprise determining the adjustment of the at least one olfactory component to be performed in order to change the olfactory state to a state corresponding to the olfactory content.

The step of determining an adjustment may comprise determining the adjustment by determining a difference in olfactory component values in the olfactory state and in the olfactory content.

The step of identifying an olfactory state may comprise determining an expected olfactory state of a predicted future location of the recipient device.

The steps of identifying an olfactory state, determining an adjustment and triggering may be performed for a plurality of recipient devices, based on common olfactory content.

The method may further comprise the steps, prior to the step of triggering, of: determining a baseline olfactory state based on the olfactory states for each one of the plurality of recipient devices; determining a baseline olfactory adjustment to be made at each recipient device to reach the baseline olfactory state; and triggering each recipient device to perform the baseline olfactory adjustment. In such a case, the step of determining a recipient olfactory adjustment, the recipient olfactory adjustment is based on determining an olfactory adjustment to be performed in order to change the baseline olfactory state to a state corresponding to the olfactory content.

The step of determining a baseline olfactory state may comprise determining an average of the olfactory states for each one of the plurality of recipient devices.

The step of triggering the recipient device to perform the recipient olfactory adjustment may comprise synchronising the olfactory content with another media content type.

According to a second aspect, it is provided an olfactory device for communicating olfactory content. The olfactory device comprises: a processor; and a memory storing instructions that, when executed by the processor, cause the olfactory device to: obtain olfactory content to be rendered at a recipient device; identify an olfactory state at the recipient device; determine an adjustment of at least one olfactory component, based on the identified olfactory state, to render the olfactory content; and trigger the recipient device to perform the adjustment of at least one olfactory component.

The instructions to determine an adjustment may comprise instructions that, when executed by the processor, cause the olfactory device to determine the adjustment of the at least one olfactory component to be performed in order to change the olfactory state to a state corresponding to the olfactory content.

The instructions to determine an adjustment may comprise instructions that, when executed by the processor, cause the olfactory device to determine the adjustment by determining a difference in olfactory component values in the olfactory state and in the olfactory content.

The instructions to identify an olfactory state may comprise instructions that, when executed by the processor, cause the olfactory device to determine an expected olfactory state of a predicted future location of the recipient device.

The olfactory device may further comprise instructions that, when executed by the processor, cause the olfactory device to execute the instructions to identify an olfactory state, determine an adjustment and trigger for a plurality of recipient devices, based on common olfactory content.

The olfactory device may further comprise instructions that, when executed by the processor, cause the olfactory device to: determine a baseline olfactory state based on the olfactory states for each one of the plurality of recipient devices; determine a baseline olfactory adjustment to be made at each recipient device to reach the baseline olfactory state; and trigger each recipient device to perform the baseline olfactory adjustment. In such a case, the instructions to determine a recipient olfactory adjustment comprise instructions that, when executed by the processor, cause the olfactory device to determine the recipient olfactory adjustment based on determining an olfactory adjustment to be performed in order to change the baseline olfactory state to a state corresponding to the olfactory content.

The instructions to determine a baseline olfactory state may comprise instructions that, when executed by the processor, cause the olfactory device to determine an average of the olfactory states for each one of the plurality of recipient devices.

The instructions to trigger the recipient device to perform the recipient olfactory adjustment may comprise instructions that, when executed by the processor, cause the olfactory device to synchronise the olfactory content with another media content type.

According to a third aspect, it is provided an olfactory device comprising: means for obtaining olfactory content to be rendered at a recipient device; means for identifying an olfactory state at the recipient device; means for determining an adjustment of at least one olfactory component, based on the identified olfactory state, to render the olfactory content; and means for triggering the recipient device to perform the adjustment of at least one olfactory component.

According to a fourth aspect, it is provided a computer program for communicating olfactory content. The computer program comprises computer program code which, when run on an olfactory device causes the olfactory device to: obtain olfactory content to be rendered at a recipient device; identify an olfactory state at the recipient device; determine an adjustment of at least one olfactory component, based on the identified olfactory state, to render the olfactory content; and trigger the recipient device to perform the adjustment of at least one olfactory component.

According to a fifth aspect, it is provided a computer program product comprising a computer program according to the fourth aspect and a computer readable means on which the computer program is stored.

According to a sixth aspect, it is provided a method for communicating olfactory content, the method being performed in an olfactory content transmitter, the olfactory content originating from a source device. The method comprises the steps of: determining a baseline olfactory state at the source device; detecting a change in olfactory state at the source device, the change being greater than a threshold; determining olfactory content based on the change in olfactory state; and transmitting the olfactory content to be rendered at a recipient device.

According to a seventh aspect, it is provided an olfactory content transmitter for communicating olfactory content originating from a source device. The content transmitter comprises: a processor; and a memory storing instructions that, when executed by the processor, cause the olfactory content transmitter to: determine a baseline olfactory state at the source device; detect a change in olfactory state at the source device, the change being greater than a threshold; determine olfactory content based on the change in olfactory state; and transmit the olfactory content to be rendered at a recipient device.

The olfactory content transmitter may be the source device.

According to an eighth aspect, it is provided an olfactory content transmitter comprising: means for determining a baseline olfactory state at a source device; means for detecting a change in olfactory state at the source device, the change being greater than a threshold; means for determining olfactory content based on the change in olfactory state, the olfactory content originating from the source device; and means for transmitting the olfactory content to be rendered at a recipient device.

According to a ninth aspect, it is provided a computer program for communicating olfactory content originating from a source device. The computer program comprises computer program code which, when run on an olfactory content transmitter causes the olfactory content transmitter to: determine a baseline olfactory state at the source device; detect a change in olfactory state at the source device, the change being greater than a threshold; determine olfactory content based on the change in olfactory state; and transmit the olfactory content to be rendered at a recipient device.

According to a tenth aspect, it is provided a computer program product comprising a computer program according to the ninth aspect and a computer readable means on which the computer program is stored.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

Embodiments presented herein improve how olfactory content is shared. This is achieved by considering the olfactory state at the receiver device of the olfactory content. Appropriate adjustments are determined to provide the olfactory content to the recipient.

Figure 1A:
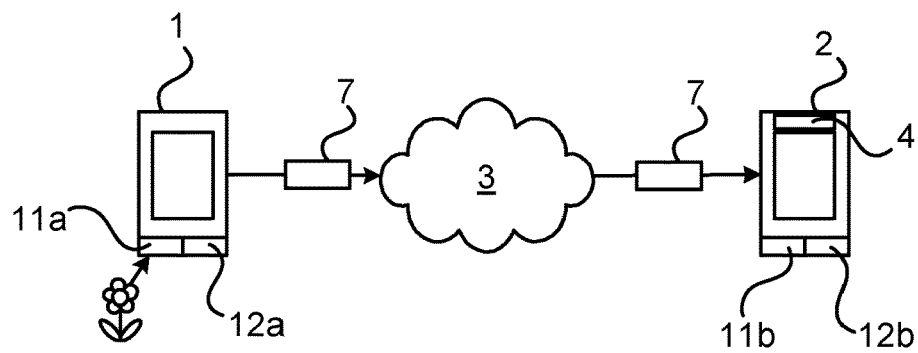
FIGS. 1A-C are schematic diagrams illustrating environments in which embodiments presented herein can be applied.
Figure 1B:
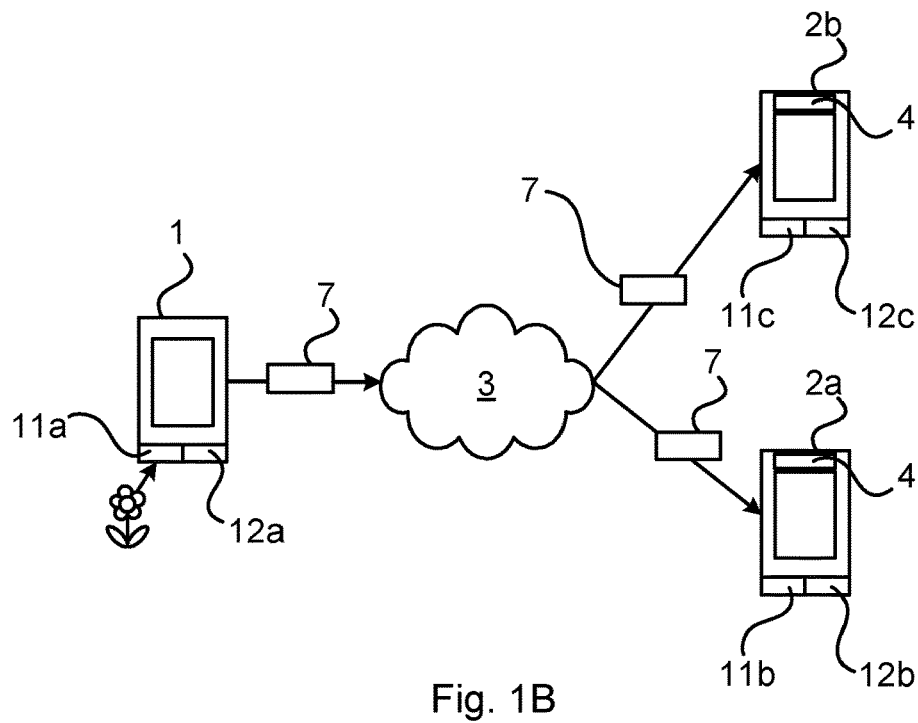
Figure 1C:
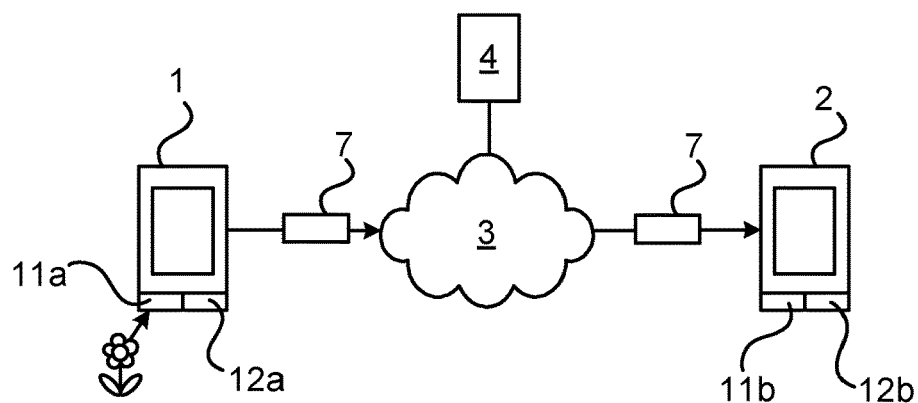

FIGS. 1A-C are schematic diagrams illustrating environments in which embodiments presented herein can be applied.

Looking first to FIG. 1A, there is an olfactory content transmitter 1. The olfactory content transmitter 1 can also be the source of the olfactory content 7 which is transmitted to a recipient device 2. Olfactory content 7 is content which represents odours, analogous to how audio content represents sound, and video content represents (moving) images.

The olfactory content transmitter 1 here comprises an olfactory sensor 11a and optionally an olfactory actuator 12a. The olfactory sensor 11a is capable of sensing odours, e.g. from a flower as illustrated, and generates representative olfactory content 7 based on the sensed odours. In one embodiment, the odour is broken down into a plurality of olfactory components, where an intensity of each olfactory component is represented by a numerical value. These component values then form part of the olfactory content 7.

Olfactory components are described in more detail in Takamichi Nakamoto, Keisuke Murakami: "Selection Method of Odor Components for Olfactory Display Using Mass Spectrum Database", Virtual Reality Conference, 2009. IEEE. Here, they analysed 104 different odours and they realized that the odours consisted of 322 different components. For example, an apple odour can be achieved by combining 9 different components. The mass spectra of the components were extracted. They then found that there are between 32-50 "basis vectors" (i.e. olfactory components) which can approximate the 104 odours. They also showed that one can approximate each of odour using only 12 to 32 components and still obtain a good classification result in a human evaluation. In another work, the authors compared odours for lime, orange, lemon, mandarin and grapefruit. They show that these odours have several components in common, while other components only exist in some of the odours.

Optionally, instead of detecting odours, the olfactory content transmitter 1 extracts odour information by analysing audio and video content which is to be transmitted to the receiver device 2. The olfactory content 7 is thus synthetized based on this analysis. For instance, if the olfactory content transmitter 1 records video and audio from a barbecue, the olfactory content transmitter can identify the barbecuing and thus synthesize olfactory content representing a barbecue smell.

In another embodiment, the olfactory content transmitter 1 allows its user to select an olfactory content to transmit in a message, e.g. in a similar way to how emojis are added to a text message. The selected olfactory content 7 then forms part of a message transmitted to the recipient device, without having been sensed by the olfactory content transmitter 1.

Optionally, olfactory content is recorded and associated with a respective location of capture, creating an olfactory content map where different locations are associated with respective olfactory content.

In one embodiment, the smell at the olfactory content transmitter 1 is detected for two points in time t1 and t2, where t2 is after t1. The olfactory content 7 is then obtained by calculating the difference between the smells at the two points in time. Due to olfactory fatigue, the complete detected current smell (at time t2) may not be what the user intends to share with the other users, but instead, the user intends to share the new smell that has started to be experienced from after time t1. The smell is measured with the olfactory sensor. By basing the olfactory content 7 on the difference in smell between t1 and t2, the olfactory state at t1 (which is probably not subjectively experienced by the user at the olfactory content transmitter 1 due to olfactory fatigue), the olfactory content 7 focuses on the new smell experienced at the olfactory content transmitter.

The olfactory content 7 is transmitted from the olfactory content transmitter 1 to the recipient device 2 via a communication network 3. The communication network 3 is any suitable communication network for digital content and can e.g. be any combination of wired and/or wireless networks. For instance, the communication network 3 can be a wide area network 6, such as the Internet, optionally also utilising IEEE 802.11x standards (also known as WiFi) or a cellular network, to allow communication with the recipient device 2. The cellular network can e.g. comply with any one or a combination of LTE (Long Term Evolution), next generation mobile networks (fifth generation, 5G), UMTS (Universal Mobile Telecommunications System) utilising W-CDMA (Wideband Code Division Multiplex), CDMA2000 (Code Division Multiple Access 2000), or any other current or future wireless network.

The recipient device 2 comprises an olfactory actuator 12b and optionally an olfactory sensor 11b. In this embodiment, the recipient device also comprises an olfactory device 4. As explained in more detail below, the olfactory device 4 uses the olfactory state at the recipient device 2 to determine what olfactory adjustments need to be made at the recipient device to render the olfactory content 7.

The olfactory content transmitter 1 and the recipient device 2 can be implemented e.g. in the form of a wireless device. The wireless device can be implemented using a smart phone, a tablet computer, laptop, etc. with wireless connectivity. The term wireless is here to be construed as having the ability to perform wireless communication. More specifically, the wireless device can comprise a number of wires for internal and/or external purposes.

FIG. 1B is a schematic diagram illustrating an environment in which embodiments presented herein can be applied for multiple recipient devices.

In this embodiment, the olfactory content 7 is again transmitted from the olfactory content transmitter 1, but is forwarded to several recipients, in this example two recipient devices 2a, 2b. Each one of the recipient devices 2a, 2b comprises an olfactory device 4.

FIG. 1C is a schematic diagram illustrating an environment in which embodiments presented herein can be applied where the olfactory device 4 does not form part of a recipient device. In this example, the olfactory device 4 can e.g. be implemented on a server or other suitable computer, and can form part of what is commonly known as 'the cloud'.

Figure 2A:
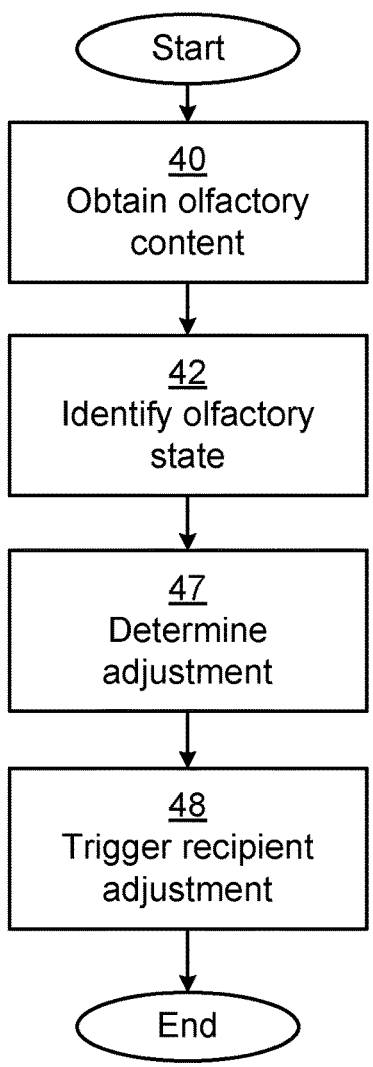
FIGS. 2A-B are flow charts illustrating embodiments of methods for communicating olfactory content, wherein the method is performed in the olfactory device of FIGS. 1A-C.
Figure 2B:
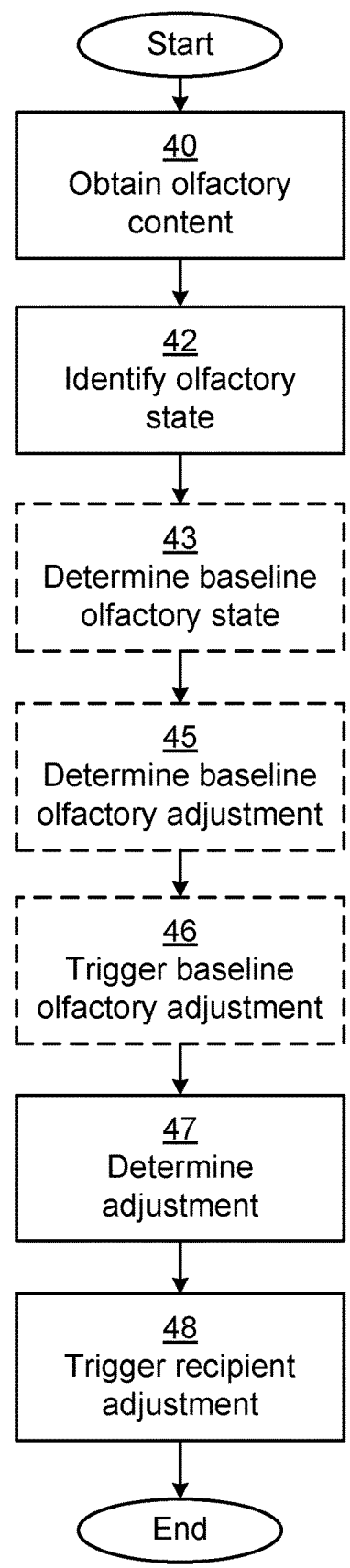

FIGS. 2A-B are flow charts illustrating embodiments of methods for communicating olfactory content 7, wherein the method is performed in the olfactory device of FIGS. 1A-C. First, the method illustrated by FIG. 2A will be described.

In an obtain olfactory content step 40, the olfactory device obtains olfactory content to be rendered at a recipient device.

In an identify olfactory state step 42, the olfactory device identifies an olfactory state at the recipient device. The olfactory state can be represented a set of intensities for a plurality of olfactory components.

If the recipient device is implemented using a mask-based device which encloses the nose of the user, the smell measurement is taken within the mask and not outside the mask to properly reflect the olfactory state experienced by the user wearing the recipient device.

When the recipient device is in movement, this step optionally comprises determining an expected olfactory state of a predicted future location of the recipient device. As an example, even though there may be a smell measured at a current location, as the user is walking towards another location, the smell will change and the new smell would be identified e.g. using the olfactory map described above.

In a determine adjustment step 47, the olfactory device determines an adjustment of at least one olfactory component, based on the identified olfactory state, to render the olfactory content. This can comprise determining the adjustment of the at least one olfactory component to be performed in order to change the olfactory state to a state corresponding to the olfactory content.

More specifically, the adjustment can be determined by determining a difference in olfactory component values in the olfactory state and in the olfactory content.

By considering the olfactory state of the recipient device for determining the adjustment, the adjustment can reduce the effects of olfactory fatigue. There are equations and tables which define how to combine certain olfactory components in order to obtain a desired smell, e.g. used in the perfume industry. Such known combinations can be used to generate the olfactory content. The equations and/or tables can be extended to include new combinations for desired olfactory content.

In a trigger recipient adjustment step 48, the olfactory device triggers the recipient device to perform the adjustment of at least one olfactory component.

When the olfactory device is implemented in the recipient device, e.g. as illustrated in FIGS. 1A-B, this trigger is implemented as an internal signal communication to perform the adjustment.

When the olfactory device is implemented external to the recipient device, e.g. as illustrated in FIG. 1C, this trigger is implemented as an external signal from the olfactory device to the recipient device via the communication network.

Optionally, this step synchronises the olfactory content with another media content type, such as video and/or audio. For instance, the olfactory content can form part of rich multimedia, where audio, video and smells are all to be rendered for a rich content consumption experience.

In one embodiment, the identify olfactory state step 42, the determine adjustment step 47 and the trigger recipient adjustment step 48 are performed for a plurality of recipient devices, based on common olfactory content.

Looking now to FIG. 2B, only new or modified steps compared to the steps of FIG. 2A will be described.

In an optional determine baseline olfactory state step 43, the olfactory device determines a baseline olfactory state based on the olfactory states for each one of the plurality of recipient devices. The baseline olfactory state can be represented a set of intensities for a plurality of olfactory components.

The baseline olfactory state can e.g. be determined as an average of the olfactory states for each one of the plurality of recipient devices. The average is then calculated individually for each olfactory component.

In an optional determine baseline olfactory adjustment step 45, the olfactory device determines a baseline olfactory adjustment to be made at each recipient device to reach the baseline olfactory state.

In an optional trigger baseline olfactory adjustment step 46, the olfactory device triggers each recipient device to perform the baseline olfactory adjustment. In this way, all the recipient devices are actuated to achieve the common baseline olfactory state. This may increase the user experience since all users subsequently start from the same baseline smell and reduce perception errors when the olfactory content is rendered. Also, this may reduce the amount of smell actuation in future sharing actions, since all recipient devices will share the same baseline. This will reduce actuation energy and use the smell substance.

In one embodiment, the baseline olfactory state is also effected at the olfactory content transmitter. If one of the current recipient devices changes role and acts as a transmitter, no new baseline olfactory adjustment is then required, since all both the previous transmitter and all recipient devices already share the same baseline olfactory state, as long as no new smell disturbance has affected individual recipients in the meantime.

When steps 43, 45 and 46 are performed, the determine adjustment step 47, comprises determining the recipient olfactory adjustment based on determining an olfactory adjustment to be performed in order to change the baseline olfactory state to a state corresponding to the olfactory content. In such a case, the same adjustment is determined for all recipient devices, since this is based on the baseline olfactory state which is common for all recipient devices.

In one embodiment, if olfactory disturbances (i.e. new smells) occur during the sharing of olfactory content and the baseline of each recipient device is modified, the smell disturbance may be measured and shared among all recipient devices so that the disturbance is compensated. This can also be applied for the baseline olfactory state, where the baseline olfactory state considers the disturbance smell.

Figure 3:
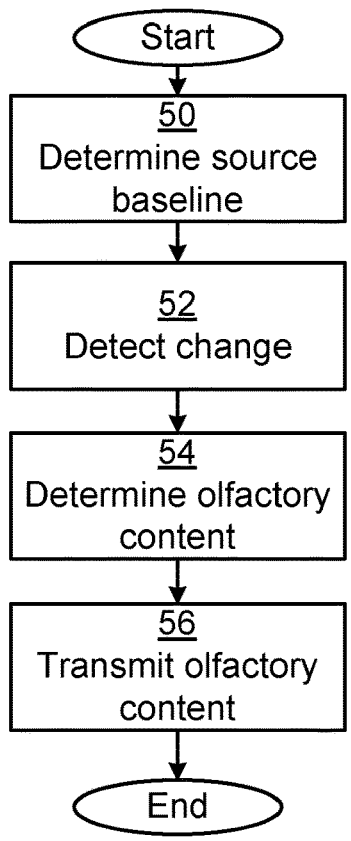
FIG. 3 is a flow chart illustrating embodiments of methods for communicating olfactory content, wherein the method is performed in the olfactory content transmitter of FIGS. 1A-C.

FIG. 3 is a flow chart illustrating embodiments of methods for communicating olfactory content, wherein the method is performed in the olfactory content transmitter of FIGS. 1A-C.

In a determine source baseline step 50, the olfactory content transmitter determines a baseline olfactory state at the source device. The source baseline can be represented a set of intensities for a plurality of olfactory components.

In a detect change step 52, the olfactory content transmitter detects a change in olfactory state at the source device, the change being greater than a threshold. This can be defined as a change greater than a threshold value in any one olfactory component or an aggregated change of all olfactory components greater than a threshold value.

In a determine olfactory content step 54, the olfactory content transmitter determines olfactory content based on the change in olfactory state. For instance, the olfactory content can be determined as a difference between a sensed olfactory state compared to the baseline olfactory state.

In a transmit olfactory content step 56, the olfactory content transmitter transmits the olfactory content to be rendered at a recipient device.

Using embodiments presented herein, the olfactory fatigue of each user is considered when performing the acquisition and rendering of olfactory content. This results in improved user experience.

An example will now be presented to illustrate an embodiment. A user A is shopping for plants and would like to share the scent of the plant with another user B which is located at home. User A reaches for the smartphone (being the olfactory content transmitter) and brings it close to the plant. User B has a smartphone (being the recipient device) with smell actuation capabilities. The olfactory state has been recorded at the smartphone of user A for a period of time, whereby it is possible to detect the specific smell of the plant as the user brings the smartphone closer to the plant, as the difference in olfactory components.

As both users do not share the same olfactory state, since user A is in a flower shop and user B is at home, a first baseline smell is released at user B's location with the baseline smell of the flower shop. The baseline smell increases the user experience since it allows user B to be immersive in the location of user A. Subsequently, the olfactory content containing the smell detected from the particular plant is released to user B. If, at this stage, user A reaches for another plant, only the smell for the new plant is to be transmitted to User B since they start from the same olfactory state.

Figure 4:
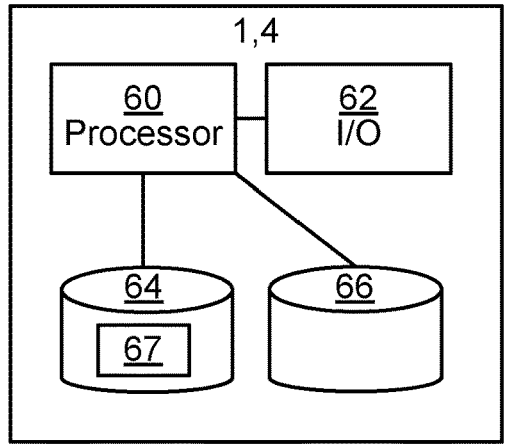
FIG. 4 is a schematic diagram illustrating components of the olfactory device and the olfactory content transmitter of FIGS. 1A-C according to one embodiment.

FIG. 4 is a schematic diagram illustrating components of the olfactory device 4 and the olfactory content transmitter 1 of FIGS. 1A-C according to one embodiment. A processor 60 is provided using any combination of one or more of a suitable central processing unit (CPU), multiprocessor, microcontroller, digital signal processor (DSP), etc., capable of executing software instructions 67 stored in a memory 64, which can thus be a computer program product. The processor 60 could alternatively be implemented using an application specific integrated circuit (ASIC), field programmable gate array (FPGA), etc. The processor 60 can be configured to execute the methods described above with reference to FIGS. 2A-B (for the olfactory device) and FIG. 3 (for the olfactory content transmitter).

The memory 64 can be any combination of random access memory (RAM) and/or read only memory (ROM). The memory 64 also comprises persistent storage, which, for example, can be any single one or combination of magnetic memory, optical memory, solid-state memory or even remotely mounted memory.

A data memory 66 is also provided for reading and/or storing data during execution of software instructions in the processor 60. The data memory 66 can be any combination of RAM and/or ROM.

An I/O interface 62 for communicating with external entities. Optionally, the I/O interface 62 also includes a user interface.

Other components are omitted in order not to obscure the concepts presented herein.

Figure 5:
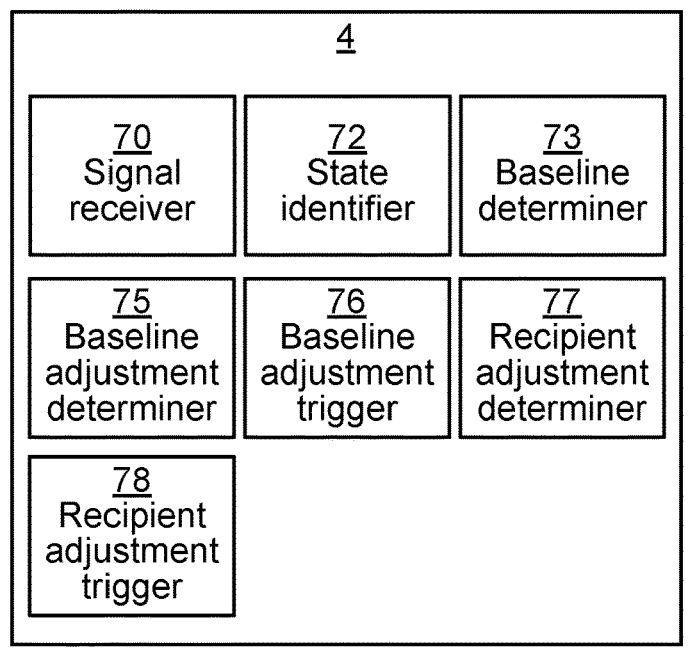
FIG. 5 is a schematic diagram showing functional modules of the olfactory device of FIGS. 1A-C according to one embodiment.

FIG. 5 is a schematic diagram showing functional modules of the olfactory device 4 of FIGS. 1A-C according to one embodiment. The modules are implemented using software instructions such as a computer program executing in the olfactory device 4. Alternatively or additionally, the modules are implemented using hardware, such as any one or more of an ASIC (Application Specific Integrated Circuit), an FPGA (Field Programmable Gate Array), or discrete logical circuits. The modules correspond to the steps in the methods illustrated in FIGS. 2A-B.

A content obtainer 70 corresponds to step 40 of FIGS. 2A-B. A state identifier 72 corresponds to step 42 of FIGS. 2A-B. A baseline determiner 73 corresponds to step 43 of FIG. 2B. A baseline adjustment determiner 75 corresponds to step 45 of FIG. 2B. A baseline adjustment trigger 76 corresponds to step 46 of FIG. 2B. A recipient adjustment determiner 77 corresponds to step 47 of FIGS. 2A-B. A recipient adjustment trigger 78 corresponds to step 48 of FIGS. 2A-B.

Figure 6:
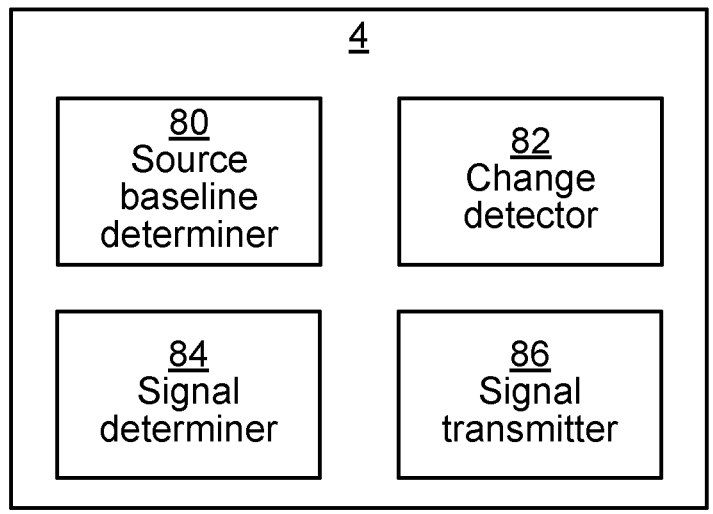
FIG. 6 is a schematic diagram showing functional modules of the olfactory content transmitter of FIGS. 1A-C according to one embodiment.

FIG. 6 is a schematic diagram showing functional modules of the olfactory content transmitter 1 of FIGS. 1A-C according to one embodiment. The modules are implemented using software instructions such as a computer program executing in the olfactory content transmitter 1. Alternatively or additionally, the modules are implemented using hardware, such as any one or more of an ASIC (Application Specific Integrated Circuit), an FPGA (Field Programmable Gate Array), or discrete logical circuits. The modules correspond to the steps in the methods illustrated in FIG. 3.

A source baseline determiner 80 corresponds to step 50 of FIG. 3. A change detector 82 corresponds to step 52 of FIG. 3. A content determiner 84 corresponds to step 54 of FIG. 3. A content transmitter 86 corresponds to step 56 of FIG. 3.

Figure 7:
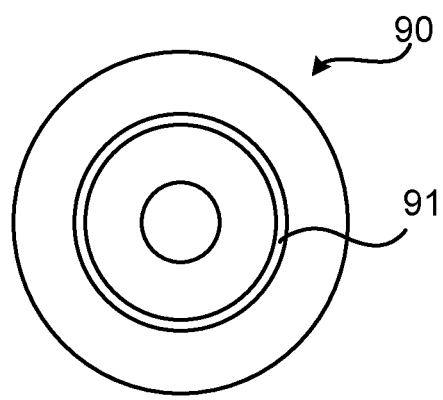
FIG. 7 shows one example of a computer program product comprising computer readable means.

FIG. 7 shows one example of a computer program product 90 comprising computer readable means. On this computer readable means, a computer program 91 can be stored, which computer program can cause a processor to execute a method according to embodiments described herein. In this example, the computer program product is an optical disc, such as a CD (compact disc) or a DVD (digital versatile disc) or a Blu-Ray disc. As explained above, the computer program product could also be embodied in a memory of a device, such as the computer program product 64 of FIG. 4. While the computer program 91 is here schematically shown as a track on the depicted optical disk, the computer program can be stored in any way which is suitable for the computer program product, such as a removable solid state memory, e.g. a Universal Serial Bus (USB) drive.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A method performed in an olfactory device, the method comprising:
    obtaining olfactory content to be rendered at a first recipient device;
    identifying an olfactory state at each of a plurality of recipient devices;
    using the identified olfactory states at the plurality of recipient devices, determining a baseline olfactory state;
    using the baseline olfactory state, determining a baseline olfactory adjustment to be performed at the first recipient device for reaching the baseline olfactory state;
    triggering the first recipient device to perform the determined baseline olfactory adjustment such that an olfactory state at the first recipient device changes to the baseline olfactory state;
    determining another olfactory adjustment to be performed at the first recipient device for reaching a state corresponding to the olfactory content; and
    triggering the first recipient device to perform said another olfactory adjustment such that an olfactory state at the first recipient device changes from the baseline olfactory state to the state corresponding to the olfactory content, wherein said another olfactory adjustment comprises adjusting at least one olfactory component.

2. The method according to claim 1, wherein the baseline olfactory adjustment and said another olfactory adjustment are determined by determining a difference in olfactory component values in the olfactory state and in the olfactory content.

3. The method according to claim 1, wherein the step of identifying an olfactory state comprises determining an expected olfactory state of a predicted future location of the recipient device.

4. The method according to claim 1, wherein the step of determining a baseline olfactory state comprises determining an average of the olfactory states for each one of the plurality of recipient devices.

5. The method according to claim 1, wherein the step of triggering the first recipient device to perform said another olfactory adjustment comprises synchronizing the olfactory content with another media content type.

6. An olfactory device comprising:
a processor; and
a memory storing instructions that, when executed by the processor, cause the olfactory device to:
obtain olfactory content to be rendered at a first recipient device;
identify an olfactory state at each of a plurality of recipient devices;
using the identified olfactory states at the plurality of recipient devices, determine a baseline olfactory state;
using the baseline olfactory state, determine a baseline olfactory adjustment to be performed at the first recipient device for reaching the baseline olfactory state;
trigger the first recipient device to perform the determined baseline olfactory adjustment such that an olfactory state at the first recipient device changes to the baseline olfactory state;
determine another olfactory adjustment to be performed at the first recipient device for reaching a state corresponding to the olfactory content; and
trigger the first recipient device to perform said another olfactory adjustment such that an olfactory state at the first recipient device changes from the baseline olfactory state to the state corresponding to the olfactory content, wherein said another olfactory adjustment comprises adjusting at least one olfactory component.

7. The olfactory device according to claim 6, wherein the baseline olfactory adjustment and said another olfactory adjustment are determined by determining a difference in olfactory component values in the olfactory state and in the olfactory content.

8. The olfactory device according to claim 6, wherein the instructions to identify an olfactory state comprise instructions that, when executed by the processor, cause the olfactory device to determine an expected olfactory state of a predicted future location of the recipient device.

9. The olfactory device according to claim 6, wherein the instructions to determine a baseline olfactory state comprise instructions that, when executed by the processor, cause the olfactory device to determine an average of the olfactory states for each one of the plurality of recipient devices.

10. The olfactory device according to claim 6, wherein the instructions to trigger the first recipient device to perform said another olfactory adjustment comprise instructions that, when executed by the processor, cause the olfactory device to synchronize the olfactory content with another media content type.

11. A computer program product comprising a non-transitory computer readable medium storing a computer program, the computer program comprising computer program code which, when run on an olfactory device, causes the olfactory device to:
obtain olfactory content to be rendered at a first recipient device;
identify an olfactory state at each of a plurality of recipient devices;
using the identified olfactory states at the plurality of recipient devices, determine a baseline olfactory state;
using the baseline olfactory state, determine a baseline olfactory adjustment to be performed at the first recipient device for reaching the baseline olfactory state;
trigger the first recipient device to perform the determined baseline olfactory adjustment such that an olfactory state at the first recipient device changes to the baseline olfactory state;
determine another olfactory adjustment to be performed at the first recipient device for reaching a state corresponding to the olfactory content; and
trigger the first recipient device to perform said another olfactory adjustment such that an olfactory state at the first recipient device changes from the baseline olfactory state to the state corresponding to the olfactory content, wherein said another olfactory adjustment comprises adjusting at least one olfactory component.

12. A wireless device comprising the olfactory device of claim 6.

13. The computer program product according to claim 11, wherein the baseline olfactory adjustment and said another olfactory adjustment are determined by determining a difference in olfactory component values in the olfactory state and in the olfactory content.

14. The computer program product according to claim 11, wherein identifying an olfactory state comprises determining an expected olfactory state of a predicted future location of the recipient device.

15. The computer program product according to claim 11, wherein determining a baseline olfactory state comprises determining an average of the olfactory states for each one of the plurality of recipient devices.

16. The computer program product according to claim 11, wherein triggering the first recipient device to perform said another olfactory adjustment comprises synchronizing the olfactory content of the first recipient device with another media content type.

* * * * *